US010835726B2

(12) United States Patent
Redding, Jr.

(10) Patent No.: US 10,835,726 B2
(45) Date of Patent: Nov. 17, 2020

(54) SYSTEMS AND METHODS FOR ENHANCING THE DELIVERY OF COMPOUNDS TO SKIN PORES USING ULTRASONIC WAVEFORMS (71) Applicant: Bruce K. Redding, Jr., Broomall, PA (US)

(72) Inventor: Bruce K. Redding, Jr., Broomall, PA (US)

(73) Assignee: BKR IP HOLDCO LLC, Broomall, PA (US)

(*) Notice: Subject to any disclaimer, the term of this patent is extended or adjusted under 35 U.S.C. 154(b) by 479 days.

(21) Appl. No.: 15/623,020

(22) Filed: Jun. 14, 2017

(65) Prior Publication Data
US 2018/0021558 A1    Jan. 25, 2018

Related U.S. Application Data (62) Division of application No. 14/006,584, filed as application No. PCT/US2012/030463 on Mar. 23, 2012, now abandoned.

(60) Provisional application No. 61/465,654, filed on Mar. 23, 2011.

(51) Int. Cl.
A61M 37/00 (2006.01)
A61B 17/00 (2006.01)

(52) U.S. Cl.
CPC ............ A61M 37/0092 (2013.01); A61B 2017/00747 (2013.01); A61B 2017/00765 (2013.01); A61M 2037/0007 (2013.01)

(58) Field of Classification Search
CPC ...... A61M 37/0092; A61M 2037/0007; A61M 35/003; A61B 2017/00747; A61B 2017/00765; A47K 7/04; A61H 23/0245
See application file for complete search history.

(56) References Cited

U.S. PATENT DOCUMENTS 4,309,989 A   1/1982   Fahim
4,372,296 A   2/1983   Fahim
4,767,402 A   8/1988   Kost et al.
(Continued)

FOREIGN PATENT DOCUMENTS

EP    1568395 A1    8/2005
WO    2006124957 A2    11/2006

OTHER PUBLICATIONS

Int'l Search Report dated May 25, 2012 in Int'l Application No. PCT/US2012/030463.
(Continued)

Primary Examiner — Manuel A Mendez
Assistant Examiner — Justin L Zamory
(74) Attorney, Agent, or Firm — Panitch Schwarze Belisario & Nadel LLP (57) ABSTRACT The invention is a device for transmitting acoustical energy through the surface of the skin of a patient, coupled with the administration of a compound, for example an acne medication, for the purpose of temporarily expanding the patient's pore size and enhancing the delivery of the compound to the patient's pores. The ultrasonic transducer emits a sonic transmission of variable intensity and frequency for the purpose of enhancing the absorption of compounds that have first been deposited onto the surface of the skin and into skin pores that have been expanded by the ultrasound transmission.

21 Claims, 9 Drawing Sheets (56) References Cited

U.S. PATENT DOCUMENTS

| | | | |
|---|---|---|---|
| 4,787,888 | A | 11/1988 | Fox |
| 4,821,740 | A | 4/1989 | Tachibana et al. |
| 4,948,587 | A | 8/1990 | Kost et al. |
| 5,007,438 | A | 4/1991 | Tachibana et al. |
| 5,016,615 | A | 5/1991 | Driller et al. |
| 5,115,805 | A | 5/1992 | Bommannan et al. |
| 5,267,985 | A | 12/1993 | Shimada et al. |
| 5,405,614 | A | 4/1995 | D'Angelo et al. |
| 5,445,611 | A | 8/1995 | Eppstein et al. |
| 5,658,247 | A | 8/1997 | Henley |
| 6,002,961 | A | 12/1999 | Mitragotri et al. |
| 6,234,990 | B1 | 5/2001 | Rowe et al. |
| 6,322,532 | B1 | 11/2001 | D'Sa et al. |
| 6,392,327 | B1 | 5/2002 | Lewis et al. |
| 6,908,448 | B2 | 6/2005 | Redding, Jr. |
| 7,440,798 | B2 | 10/2008 | Redding, Jr. |
| 2005/0038377 | A1 | 2/2005 | Redding |
| 2007/0020321 | A1* | 1/2007 | Redding ................ A61K 9/703 424/447 |
| 2007/0060864 | A1* | 3/2007 | Redding ........... A61M 37/0092 604/22 |
| 2009/0318852 | A1* | 12/2009 | Reed ................... A61M 35/003 604/22 |

OTHER PUBLICATIONS

Int'l Written Opinion dated Oct. 3, 2013 in Int'l Application No. PCT/US2012/030463.
Int'l Preliminary Report on Patentability dated Oct. 3, 2013 in Int'l Application No. PCT/US2012/030463.
Office Action dated May 11, 2016 in Redding U.S. Appl. No. 14/006,584.

* cited by examiner

SYSTEMS AND METHODS FOR ENHANCING THE DELIVERY OF COMPOUNDS TO SKIN PORES USING ULTRASONIC WAVEFORMS

CROSS REFERENCE TO RELATED APPLICATION(S)

This application claims the benefit of is a 371 National Filing of International Patent application Patent Application No. PCT/US2012/030463, filed Mar. 23, 2012, which claims priority to U.S. Provisional Application No. 61/465,654, filed 23 Mar. 23, 2011, the entire contents of which are hereby incorporated herein by reference as if fully set forth in their entireties.

FIELD OF THE INVENTION

The present invention relates generally to systems and methods for enhancing the delivery of compounds to skin pores using ultrasonic waveforms, and more particularly to the use of sonic transmission of variable intensity and frequency to dilate a patient's skin pores and deliver a compound to the dilated pores.

BACKGROUND OF THE INVENTION

It is known in the art to utilize ultrasound to enhance the permeability of the skin and synthetic membranes to drugs and other molecules. Ultrasound is typically generated by vibrating a piezoelectric crystal or other electromechanical element by passing an alternating current through the material. The use of ultrasound to increase the permeability of the skin to drug molecules has been termed sonophoresis or phonophoresis. It is also known in the art to: use ultrasound to assist with the massaging of topical applications of medications into the skin; control the infusion of molecules that have been incorporated in a coupling agent or that are applied through a transdermal patch through the skin using ultrasound; and deliver drugs transbuccally using ultrasound. Relevant prior art references include U.S. Pat. Nos. 4,309,989, 4,372,296, 4,767,402, 4,821,740, 4,948,587, 5,007,438, 5,016,615, and 5,115,805.

While the use of ultrasound for drug delivery is known, results have been largely disappointing in that enhancement of skin permeability has been relatively low. There is currently no consensus on the efficacy of ultrasound for increasing drug flux across the skin. There has also been a lack of focus in the prior art on the power utilization of the sonic transducer and the size of the sonic device.

Other methods of increasing the permeability of skin to drugs have been described, such as the use of iontophoresis. Iontophoresis involves the application of an external electric field and topical delivery of an ionized form of drug or a unionized drug carried with the water flux associated with ion transport (electro-osmosis). Drawbacks to the use of iontophoresis are the difficulties in controlling drug delivery and irreversible skin damage caused by use of the technique.

Thus, there is a need for improved systems and methods for enhancing the delivery efficacy of compounds to skin pores using ultrasonic waveforms.

SUMMARY OF THE INVENTION

In one respect, the present invention comprises a method for delivering a compound to human skin, the method comprising: (a) depositing the compound at a treatment site on a surface of the skin; and (b) directing an ultrasound waveform consisting of at least one non-sinusoidal waveform having a frequency in the range of 18 kHz to 175 kHz into the skin at at least a portion of the treatment site using an ultrasonic device.

In another respect, the present invention comprises a method for delivering a compound to human skin, the method comprising: (a) depositing the compound at a treatment site on a surface of the skin; and (b) driving the compound into at least a portion of an epidermal layer of the skin at a treatment site without any significant portion of the compound penetrating a dermal layer of the skin by directing an ultrasound waveform consisting of at least one non-sinusoidal waveform into the skin at at least a portion of the treatment site.

In yet another respect, the present invention comprises a method for delivering an acne-treatment compound into human skin, the method comprising: (a) depositing the acne-treatment compound at a treatment site on a surface of the skin, wherein at least one pore is located in the skin at the treatment site; (b) dilating the at least one pore using a first waveform; and (c) driving the acne compound into at least a portion of an epidermal layer of the skin at a treatment site without any significant portion of the compound penetrating a dermal layer of the skin using a second waveform.

In still another respect, the present invention comprises an apparatus comprising an ultrasonic transducer having at least one transducer and a driving circuit that is operationally configured to emit an ultrasonic waveform that alternates between a first waveform and a second waveform, both the first waveform and the second waveform being non-sinusoidal; and a pad that is removably attached to the ultrasonic transducer, the pad being vibrated by the ultrasonic waveform when it is attached to the ultrasonic transducer, the pad being designed to come into contact with a treatment site on a person's skin.

Further aspects of the invention include:

Aspect 1. A method for delivering a compound to human skin, the method comprising: (a) depositing the compound at a treatment site on a surface of the skin; and (b) directing an ultrasound waveform consisting of at least one non-sinusoidal waveform having a frequency in the range of 18 kHz to 175 kHz into the skin at at least a portion of the treatment site using an ultrasonic device.

Aspect 2. The method of any one of Aspects 1 and 3-14, wherein each of the at least one non-sinusoidal waveform has a frequency in the range of 20 kHz to 100 kHz.

Aspect 3. The method of any one of Aspects 1, 2, and 4-14, wherein step (b) further comprises directing an ultrasound waveform consisting of at least one non-sinusoidal waveform having a frequency in the range of 18 kHz to 175 kHz into the skin at least a portion of the treatment site using an ultrasonic device in a manner that results in at least some of the compound penetrating at least a portion of an epidermal layer of the skin and no significant portion of the compound penetrating a dermal layer of the skin.

Aspect 4. The method of any one of Aspects 1-3 and 5-14, wherein the at least one-sinusoidal waveform comprises a sawtooth waveform.

Aspect 5. The method of any one of Aspects 1-4 and 6-14, wherein the at least one-sinusoidal waveform an alternating waveform that alternates between a first waveform for a first predetermined period and a second waveform for a second predetermined period, the second waveform being different from the first waveform.

Aspect 6. The method of any one of Aspects 1-5 and 7-14, wherein the at least one-sinusoidal waveform is an alternating waveform that alternates between a sawtooth waveform for a first period and a second waveform for a second period, the second waveform being different from the sawtooth waveform.

Aspect 7. The method of any one of Aspects 1-6 and 8-14, wherein the first period is of a longer duration than the second period.

Aspect 8. The method of any one of Aspects 1-7 and 9-14, wherein the duration of the first predetermined period is at least twice the duration of the second predetermined period.

Aspect 9. The method of any one of Aspects 1-8 and 10-14, wherein the duration of the first predetermined period is at least four times the duration of the second predetermined period.

Aspect 10. The method of any one of Aspects 1-9 and 11-14, wherein the duration of the first predetermined period is about 80 milliseconds and the duration of the second predetermined period is about 20 milliseconds.

Aspect 11. The method of any one of Aspects 1-10 and 12-14, wherein step (a) further comprises depositing the compound at a treatment site on a surface of the skin, wherein the compound comprises a pharmaceutical compound for the treatment of acne.

Aspect 12. The method of any one of Aspects 1-11, 13, and 14, wherein step (b) further comprises directing an ultrasound waveform consisting of at least one non-sinusoidal waveform having a frequency in the range of 18 kHz to 175 kHz into the skin at least a portion of the treatment site using an ultrasonic device having at least one transducer, wherein each of the at least one transducers is operated at an intensity in the range of 75 mW/sq·cm to 150 mW/sq·cm.

Aspect 13. The method of any one of Aspects 1-12 and 14, wherein step (a) comprises depositing the compound at a treatment site on a surface of the skin, wherein the skin is located on a human face.

Aspect 14. The method of any one of Aspects 1-13, wherein the compound comprises an acne treatment medication.

Aspect 15. A method for delivering a compound to human skin, the method comprising: (a) depositing the compound at a treatment site on a surface of the skin; and (b) depositing the compound at a treatment site on a surface of the skin; and driving the compound into at least a portion of an epidermal layer of the skin at a treatment site without any significant portion of the compound penetrating a dermal layer of the skin by directing an ultrasound waveform consisting of at least one non-sinusoidal waveform into the skin at at least a portion of the treatment site.

Aspect 16. The method of any one of Aspects 15 and 17-19, wherein each of the at least one non-sinusoidal waveforms has a frequency in the range of 18 kHz to 175 kHz.

Aspect 17. The method of any one of Aspects 15, 16, 18, and 19, wherein the ultrasound waveform consists of an alternating waveform consisting of a sawtooth waveform provided for a first period and a square waveform provided for a second period that is no more than one half of the first period.

Aspect 18. The method of any one of Aspects 15-17 and 19, wherein the first period is about 80 milliseconds and the second period is about 20 milliseconds.

Aspect 19. The method of any one of Aspects 15-18, wherein step (b) further comprises generating the ultrasonic waveform using an ultrasonic device having at least one transducer, wherein each of the at least one transducers is operated at an intensity in the range of 75 mW/sq·cm to 150 mW/sq·cm.

Aspect 20. A method for delivering an acne-treatment compound into human skin, the method comprising: (a) depositing the acne-treatment compound at a treatment site on a surface of the skin, wherein at least one pore is located in the skin at the treatment site; (b) dilating the at least one pore using a first waveform; and (c) driving the acne compound into at least a portion of an epidermal layer of the skin at a treatment site without any significant portion of the compound penetrating a dermal layer of the skin using a second waveform.

Aspect 21. The method of any one of Aspects 20 and 22-25, wherein step (b) comprises dilating the at least one pore using a first waveform consisting of a sawtooth waveform.

Aspect 22. The method of any one of Aspects 20, 21, and 23-25, wherein step (c) comprises dilating the at least one pore using a first waveform consisting of a square waveform.

Aspect 23. The method of any one of Aspects 20-22, 24, and 25, further comprising: (d) sequentially and repeatedly performing step (b) for a first duration and step (c) for a second duration, wherein the first duration is at least twice as long as the second duration.

Aspect 24. The method of any one of Aspects 20-23 and 25, further comprising: (d) sequentially and repeatedly performing step (b) for about 80 milliseconds and step (c) for about 20 milliseconds.

Aspect 25. The method of any one of Aspects 20-24, wherein the first waveform and the second waveform each have a frequency in the range of 18 kHz to 175 kHz.

Aspect 26. An apparatus comprising: an ultrasonic transducer having at least one transducer and a driving circuit that is operationally configured to emit an ultrasonic waveform that alternates between a first waveform and a second waveform, both the first waveform and the second waveform being non-sinusoidal; and a pad that is removably attached to the ultrasonic transducer, the pad being vibrated by the ultrasonic waveform when it is attached to the ultrasonic transducer, the pad being designed to come into contact with a treatment site on a person's skin.

Aspect 27. The apparatus of any one of Aspects 26 and 28-32, wherein the first waveform is a sawtooth waveform and the second waveform is a square waveform.

Aspect 28. The apparatus of any one of Aspects 26, 27, and 29-32, wherein the first waveform has a first predetermined period and the second waveform has a second predetermined period, the first and second predetermined periods being of different duration.

Aspect 29. The apparatus of any one of Aspects 26-28 and 30-32, wherein the duration of the first period is at least twice the duration of the second period.

Aspect 30. The apparatus of any one of Aspects 26-29, 31, and 32, wherein the duration of the first period is at least four times the duration of the second period.

Aspect 31. The apparatus of any one of Aspects 26-30 and 32, wherein the duration of the first period is approximately 80 milliseconds and the duration of the second period is approximately 20 milliseconds.

Aspect 32. The apparatus of any one of Aspects 26-31, wherein the pad contains a compound including a medication for the treatment of acne.

Still further aspects and objects of the invention are detailed below.

One object of the invention is to provide a portable ultrasonic drug delivery device suitable for applying ultrasound to skin pores for controlling delivery of drugs, nutrients, and other molecules into the skin tissue or pores.

Another object of the invention is a Class V flextensional cymbal transducer and transducer array for use in the device to deliver low frequency ultrasound in a portable device at high efficiency for delivery of compounds and therapeutic applications following deposition of a medication compound which has been deposited onto the face or skin.

These and other objects of the inventions can be accomplished by applying various ultrasound frequencies, intensities, amplitudes and/or phase modulations to control the magnitude of the ultrasound signal to achieve a therapeutic or nutritional level.

One aspect of the programmability and flux control is the ability to optimize therapeutic delivery for an individual patient (such examples may include patients that are at different stages of a disease, elderly patients, young, juvenile, or based on gender).

Another aspect is to optimize delivery for each drug. The molecular structure of each biologically active molecule is different and responds differently to ultrasound. Control of the frequency, intensity, concentration, timing of delivery, drug regimen can optimize delivery of each drug type.

This invention demonstrates a method of multiple array transducers that changes the area of the skin used for drug absorption, especially to the pores of the skin.

A further aspect of the invention is the transducer or array of transducers built into the ultrasonic applicator device.

A preferred aspect of the invention is the use of the transducer device for the delivery of skin care compounds and medication, particularly aimed at the treatment of acne, but may also be applicable to a broader drug delivery system.

Another embodiment of the invention is the use of phase modulation, alternating waveforms, and frequency modulation to achieve more effective ultrasonic delivery of compounds and to increase the rate of delivery of drug compounds.

Additional objects, advantages and novel features of the invention will be set forth in part in the description which follows, and in part will become apparent to those skilled in the art upon examination of the following, or may be learned by practice of the invention.

BRIEF DESCRIPTION OF THE DRAWINGS

The present invention will hereinafter be described in conjunction with the appended drawing figures, wherein like numerals denote like elements.

FIG. 1 illustrates the structure of human skin;

FIG. 2A is a schematic drawing of the structure of acne infected skin pores;

FIG. 2B is a schematic drawing of the effect of ultrasound upon acne infected skin pores;

FIG. 3 is a schematic drawing of the primary mode of operation for the present invention to dilate skin pores to enable compounds to be more easily deposited therein;

FIG. 4 is a diagram showing pore enlargement using ultrasound under three different sets of conditions;

FIG. 5 is a photograph of the epidermal layer of the skin, which shows the ability of ultrasound treatment to delivery drugs only to the skin pores and not to the surrounding tissue;

FIGS. 6A and 6B are co-focal images of the skin, before and after, respectively, a sixty second application of ultrasound, showing the dilation of skin pores as a result thereof;

FIG. 7 shows an exemplary alternating ultrasound waveform that may be used in conjunction with the herein disclosed systems and methods;

FIG. 8 shows an ultrasound device in accordance with the present invention;

FIG. 9 shows a protective and sanitary cap that may be placed on the ultrasound device;

FIG. 10 is a partial exploded view of the ultrasound device of FIG. 8, showing some of its internal components;

FIG. 11 is a partial exploded view of the ultrasound device of FIG. 8, showing some of its internal components;

FIG. 12 is an exploded view of a first exemplary transducer assembly for the ultrasound device;

FIG. 13 is an exploded view of a second exemplary transducer assembly for the ultrasound device; and FIGS. 14A-C are tables showing porphyrin count reduction in three respective volunteers at days 1, 15, and 30 of a trial after using an ultrasound device according to the present invention.

DETAILED DESCRIPTION OF THE PREFERRED EMBODIMENTS

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. It should be understood that various changes may be made in the function and arrangement of elements without departing from the spirit and scope of the invention, as set forth in the appended claims.

To aid in describing the invention, directional terms may be used in the specification and claims to describe portions of the present invention (e.g., upper, lower, left, right, etc.). These directional definitions are merely intended to assist in describing and claiming the invention, and are not intended to limit the invention in any way. In addition, reference numerals that are introduced in the specification in association with a drawing figure may be repeated in one or more subsequent figures without additional description in the specification in order to provide context for other features.

The articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all, indiscriminately of whatever quantity. The term "and/or" placed between a first entity and a second entity means one of (1) the first entity, (2) the second entity, and (3) the first entity and the second entity. The term "and/or" placed between the last two entities of a list of 3 or more entities means at least one of the entities in the list.

In the claims, letters may be used to identify claimed steps (e.g., (a), (b), and (c)). These letters are used to aid in referring to the method steps and are not intended to indicate the order in which claimed steps are performed, unless and only to the extent that such order is specifically recited in the claims.

For purposes of this application, the terms "ultrasound" or "ultrasonic" means mechanical pressure waves with frequencies above 15 kHz.

For purposes of this application, the terms "compound" or "composition" means a substance having one or more ingredients.

For purposes of this application, the terms "sawtooth" or "sawtooth waveform" means any non-sinusoidal waveform, including but not limited to sawtooth, reverse sawtooth, and triangle waveforms, but excluding only a square waveform.

The present application teaches systems and methods for providing a portable ultrasonic delivery device, which is held by the patient or by a medical professional, and is applied over the skin of a patient for the purpose of enhancing the delivery of a compound, thereby increasing its delivery bioabsorption and pharmacokinetics. The ultrasonic delivery device may being programmed to deliver an ultrasonic signal through the head of the device directly to the skin pores, for the purpose of dilating the skin pores and pushing or forcing a dose of medication further within the tissue. It is an object of the present invention to provide a small, wieldable ultrasonic device. To achieve this goal, the transducers within the device are preferably small, compact, and battery-powered.

In one exemplary embodiment, the compound that is to be moved into the skin pores is an acne medication, for example a bactericide such as benzoyl peroxide. Use of an ultrasonic device to dilate the pores and mechanically push the compound into the pores more effectively delivers the compound to the acne-infected pores than does simple topical application of the compound to the skin. Once deposited within the pores by the acoustical energy, the bactericide compound is able to more quickly reduce the prevalence of the pore infections (i.e., acne). In this way, treatment of acne can occur in a shorter period of time and with fewer and lower-volume applications of the compound to the skin.

The present invention is a combination therapy method that involves one or more of the following steps: (1) applying acoustical energy, which could be either simple vibration or ultrasonic energy, to a treatment site on the skin to enlarge or dilate the pores; (2) applying acoustical energy, which could be either simple vibration or ultrasonic energy, to the pores, whereby the sonic transmission helps to evacuate the pore of trapped or infected skin oils, which may be the cause of acne infection, through the use of mechanical pressure; (3) placing a compound, for example an acne medication (which may in the form of a serum, solution, cream, paste, gel, or lotion), on a treatment site on the skin, then applying acoustical energy, which could be either simple vibration or ultrasonic energy, to the compound for the purpose of increasing the absorption of the compound directly within the pores by mechanically depositing or pushing the compound into the pores; (4) applying acoustical energy, which could be either simple vibration or ultrasonic energy, to a treatment site on the skin in order to provide an enhanced surface treatment area on the skin to reduce the formation of bacteria or the adherence of bacteria on the surface of the skin, to destroy the bacteria directly using the acoustical energy, or to assist with the application of a bactericide or other compound to the skin; and (5) optionally placing a compound, for example an acne medication (which may in the form of a serum, solution, cream, paste, gel, or lotion), on a treatment site on the skin, then applying acoustical energy, which could be either simple vibration or ultrasonic energy, to the skin, wherein the acoustical energy (with or without the use of a medication) provides a medium within the skin which retards the formation of skin lesions, infections, blackheads, whiteheads, pustules, or other skin disorders, including acne. In step (5), acoustical energy is used to irradiate the skin with energy sufficient to reduce or impede the formation of skin lesions or infections either by the use of the acoustical energy itself or in combination with a cleanser, moisturizer, medication, or other compound. In some embodiments, the treatment site may be located on a human face.

Figure 1:
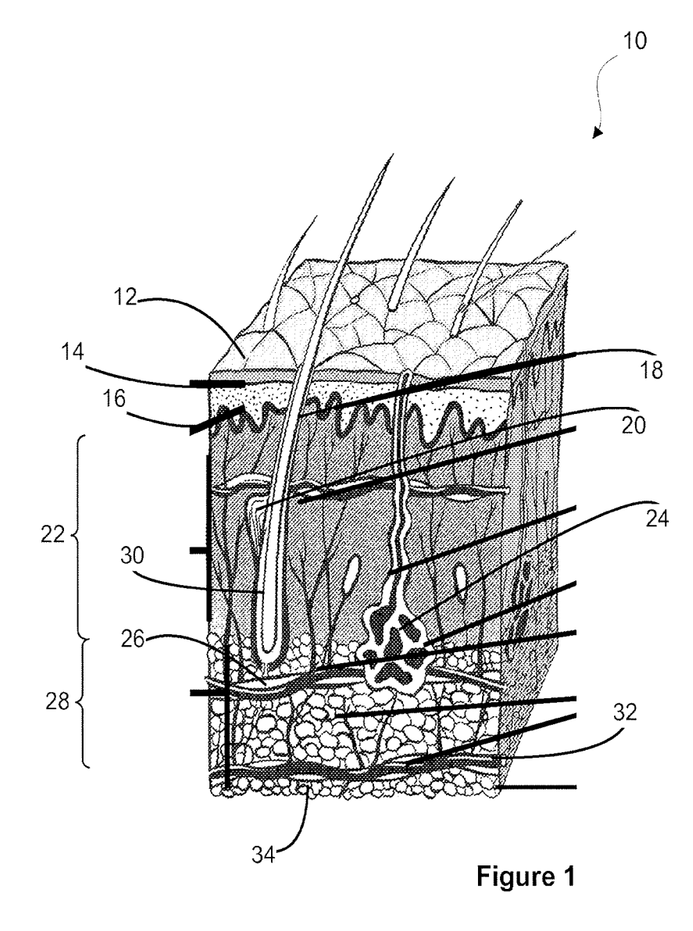

Referring to FIG. 1, a cross-section of human skin 10 is shown. The epidermis layer 12 comprises the stratum corneum 14 and the viable epidermis 16. Skin pores 41 (see FIG. 2) are located in the epidermis layer 12. Below the epidermis layer 12 is the dermis layer 22, which includes hair follicles 18, sebaceous glands 20, eccrine sweat glands 24, and hair roots 30. Below the dermis layer 22 is the subcutaneous connective tissue 28, which comprises a vascular network 32, subcutaneous fat 34, and apocrine sweat glands 26.

Figure 2A:
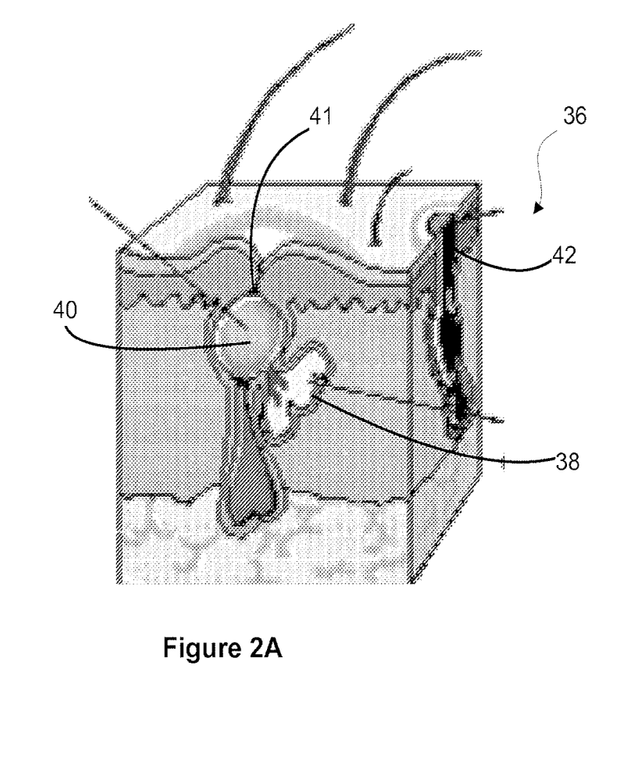
Figure 2B:
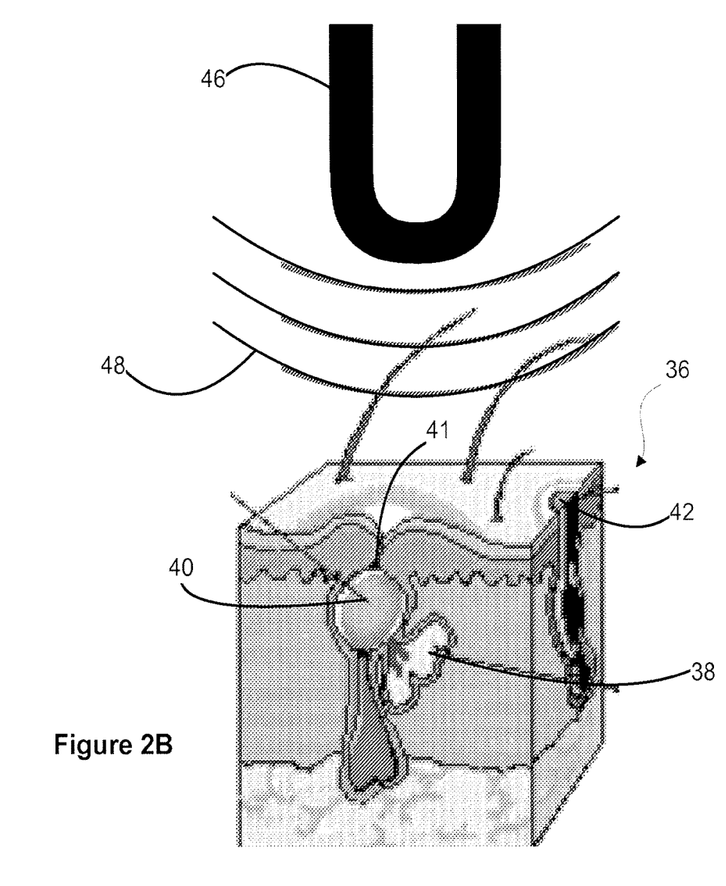

In FIG. 2A, an infected pimple 40 within a cross-section of human skin 36 is shown. Oil gland 38 is connected to the skin pore 41. In this Figure, the skin pore 41 is shown filled with bacteria. A black head 42, which constitutes another type of bacterial infection, is also shown. FIG. 2B shows the infected pimple 40 being treated with acoustic waves 48 from an ultrasound emitter 46, which may be ultrasound device 62 (see FIGS. 8-12).

A first exemplary method according to the present invention may comprise the steps listed below. First, the vibrational effects of the ultrasound act to gently evacuate the standing oil from the pore 41. Due to the unique alternating ultrasound waveform 56 (see FIG. 7) employed by the present invention—which will be discussed in further detail below—no heat or cavitation effects are applied to the skin. This is an improvement over conventional ultrasound methods, which typically employ sinusoidal waveforms.

Second, a sawtooth waveform 58 of the alternating ultrasound waveform 56 acts to expand the size of the skin pore 41. The acne-fighting medication or other compound may be applied to the face either before or after this step. Applicant has found that in approximately ten seconds, the sawtooth waveform 58 of the alternating ultrasound waveform 56 of the ultrasonic transmission can dilate or expand the facial pores to a size whereupon the pore is more reticent to receive the compound (e.g., an anti-acne medication). Often times, when topically applied by hand, topical compounds such as creams, lotions, and pastes tend to smear across the face, remaining only on the surface of the affected pore but not penetrating therein. With a pore that has been dilated according to the present invention, the compound can be more readily deposited into the interior of the pore itself. The ultrasound treatment according to the present invention, particularly the sawtooth waveform 58 component of the alternating ultrasound waveform 56, acts as the dilation mechanism that makes the pore "hole" larger. Once dilated, the opened pores form a delivery pathway which enables the anti-acne formulations or other compounds to be deposited directly into the pore interior, deep below the skin's surface.

Figure 3:
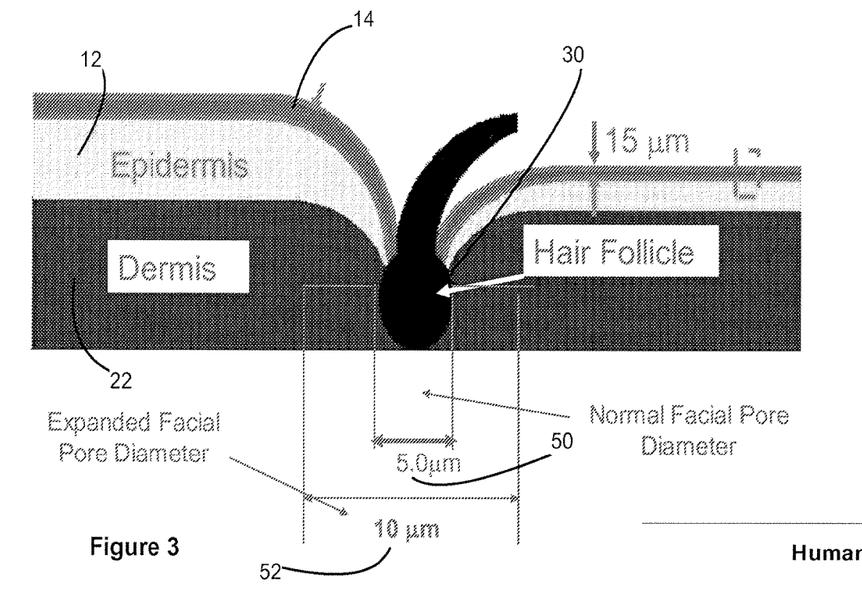
Figure 6A:
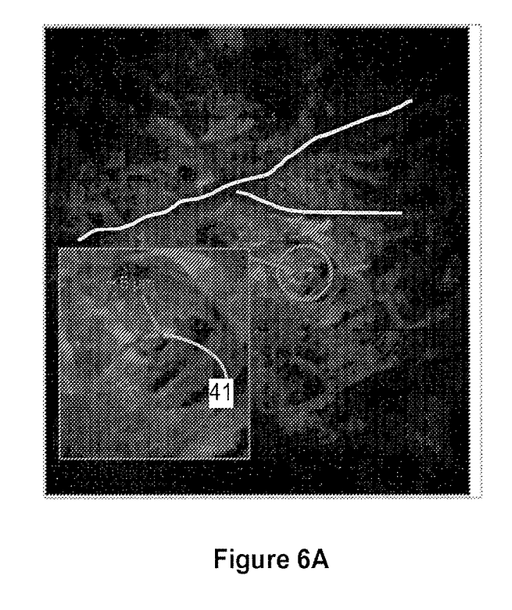
Figure 6B:
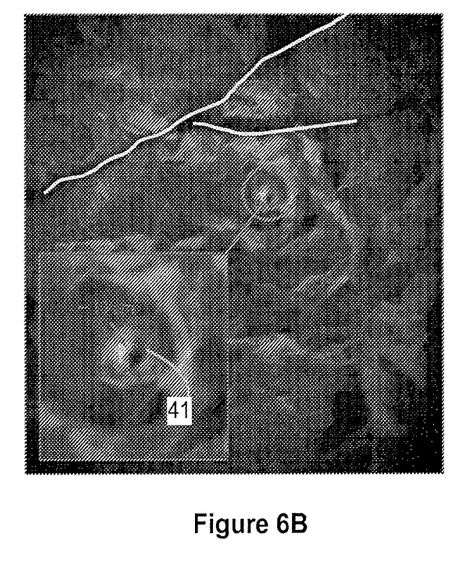

FIG. 3 shows the effect of the use of the sawtooth waveform 58 on the size of skin pores. When exposed to the sawtooth waveform 58 of the alternating ultrasound waveform 56, normal facial pore diameter 50, which typically measures on the order of 5 microns, is increased to an expanded facial pore diameter 52 of approximately 10 microns. FIGS. 6A and 6B are co-focal images of the skin, respectively, before and after a sixty second application of ultrasound in accordance with the present invention, showing the dilation of skin pore 41 from approximately 5 microns to approximately 10 microns as a result thereof FIGS. 6A and 6B are fluorescence images of an area 500 microns by 500 microns. FIG. 6B was taken one hour after the ultrasound treatment. Applicant's experiments have shown that average pore size will return to normal size within several hours after treatment with the ultrasound device according to the present invention.

Figure 4:
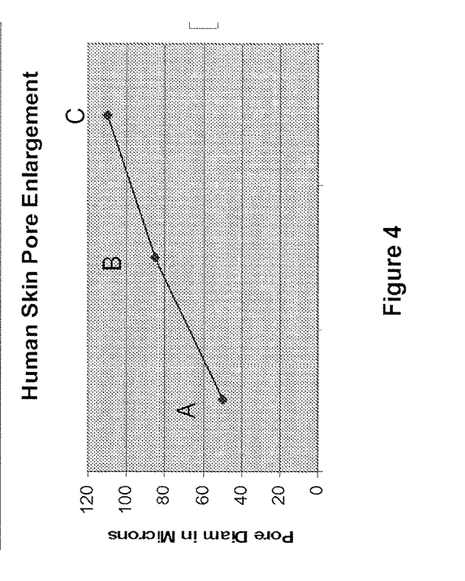

FIG. 4 is a diagram showing pore enlargement using ultrasound according to the present invention under three different sets of conditions A, B, and C. Set A shows the size of normal abdominal skin pores of approximately 50 microns prior to any ultrasonic treatment. Set B shows skin pore enlargement using a total power output of the ultrasound device of 125 mW/sq. cm at an acoustic frequency of 30 kHz. The average pore diameter has been increased to approximately 85 microns. Set C shows skin pore enlargement using a total power output of the ultrasound device of 225 mW/sq. cm at an acoustic frequency of 30 kHz. The average pore diameter has been increased to approximately 110 microns. Based on the size of the particles of the compound that need to be delivered to the pores, as further discussed below, the parameters of the ultrasonic signal can be varied accordingly.

Turning back to the exemplary method described above, in a third step, a square waveform 60 component of the alternating ultrasound waveform 56 (see FIG. 7) acts to force the acne medication or other compound down within the interior of the pore 41. In accordance with the present invention, the square waveform 60 mechanically pushes the medication deep into the pore 41, but also into the surround epidermal tissue, thereby delivering the compound to the stratum corneum 14 far more effectively than does manual, topical application of the compound.

Finally, the now treated pore 41, having been both evacuated of oil and penetrated with the acne-fighting compound, can, along with the surrounding skin area, which has also been filled with the acne-fighting compound, better fight any existing skin infections and more easily ward off any additional bacterial or other skin infections.

Figure 5:
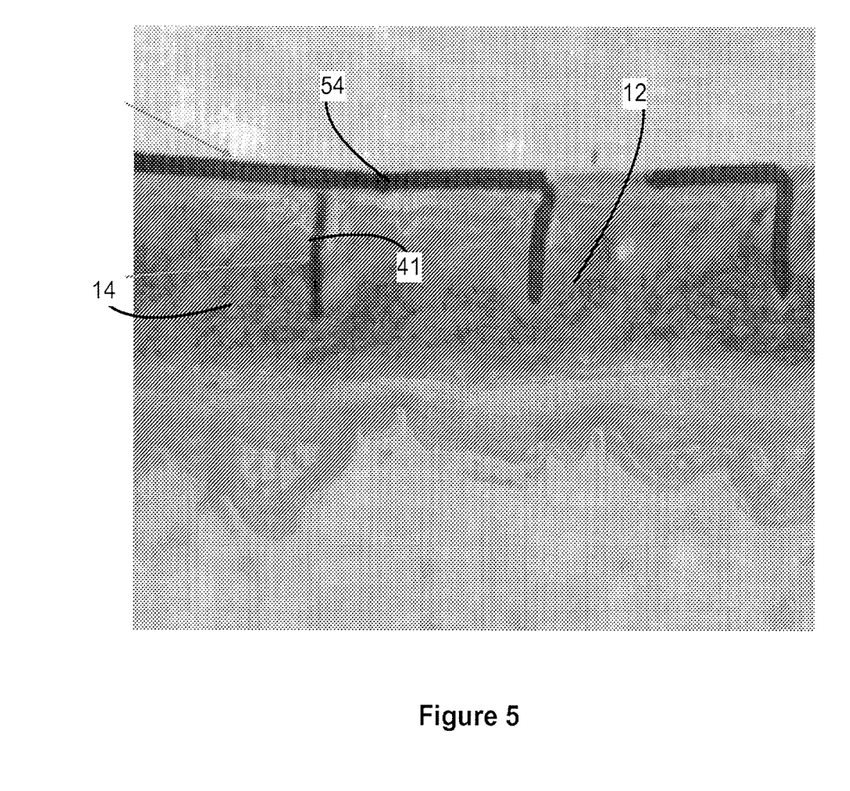

In many applications, it may be desirable to limit the placement of the compound to the epidermis layer 12 (i.e., to the pores 41 and stratum corneum 14) so that no transdermal deposition of the compound occurs. Referring now to FIG. 5, Applicant performed a test on human skin in vivo involving the deposition of a marker dye as part of a compound 54 on the epidermis layer 12 of a patient. After using the ultrasound device 62 according to the present invention to open the pores 41 and push the compound 54 into the pores 41, the image of FIG. 5 was taken. The results show that the ultrasound device 52 limited penetration of the compound 54 to the pores 41 and stratum corneum 14, but did not result in the compound 54 being driven below the epidermis layer 12.

The parameters of ultrasound that can be changed to improve or control penetration of the drug after it has been delivered include: (1) frequency; (2) intensity; (3) waveform; and (4) time of exposure. All of these parameters may be modulated simultaneously in a complex fashion to increase the effect or efficiency of the ultrasound as it relates to enhancing the movement of compounds into the pores.

Figure 7:
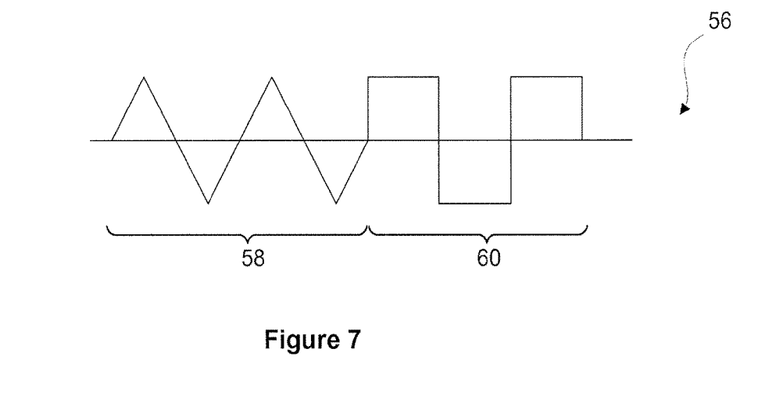
Figure 8:
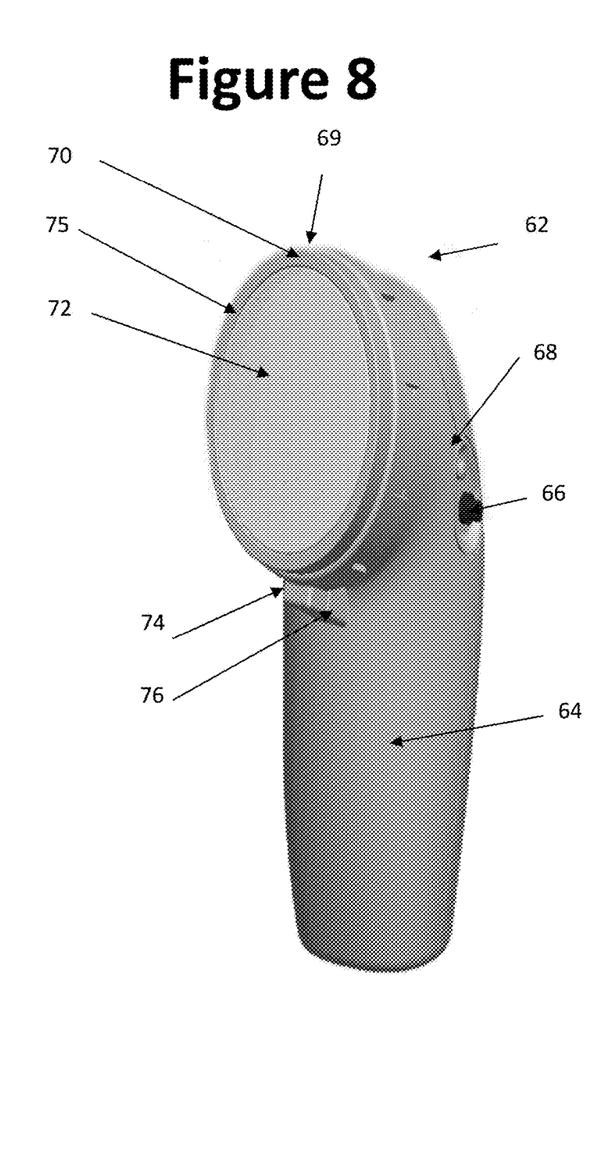
Figure 9:
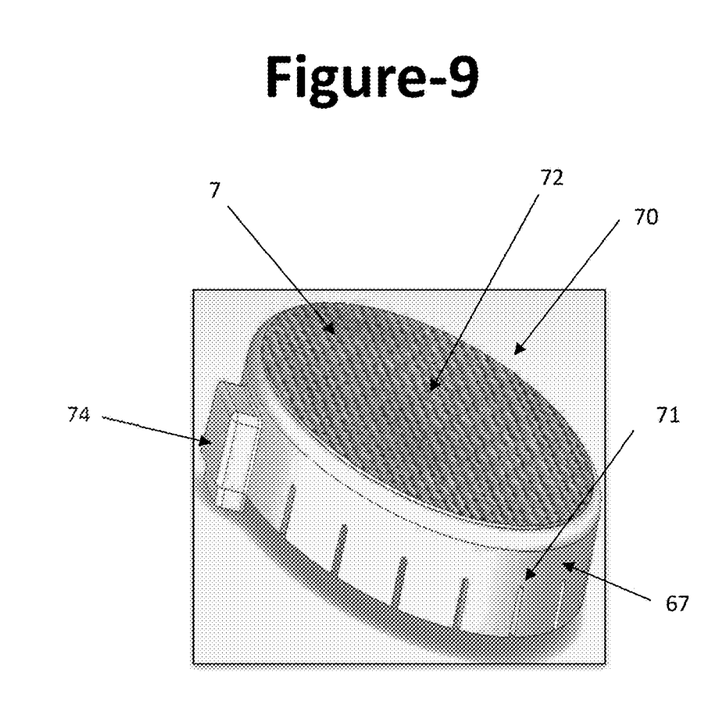

The ultrasonic device 62 according to the present invention is designed to provide alternating wave forms of sonic energy to the skin, converting ideally between sawtooth waveform and square waveform. Applicant has discovered that the sawtooth waveform is effective at enlarging the size of the pore channel while the square waveform provides the ramming force needed to push the deposited medication into the pore 41. FIG. 7 shows an exemplary alternating ultrasound waveform 56, which is comprised of a sawtooth waveform 58 and a square waveform 60. Applicants discovered unexpectedly that those frequencies within the particular range of between approximately 18-175 kHz for the sawtooth waveform works to dilate the pores of the skin. Frequencies outside of this range do not work well, if at all. In fact, Applicant found that frequencies above approximately 175 kHz would begin to constrict the size of the pores of the skin, which would frustrate the purpose of the present invention. In some embodiments, the preferred range of frequencies may be in the range of approximately 20-100 kHz.

The use of sinusoidal waveform ultrasound is not desired because sine wave ultrasound tends to develop microbubbles in the skin and in the deposited compound by a process called cavitation. Cavitation could overheat the drug and cause it to denature. Excessive heating can also lead to skin irritation, discoloration, or burning. The use of alternating wave forms of sonic energy from sawtooth waveform 58 to square waveform 60 avoids cavitation by avoiding the generation of thermal energy. Just when cavitation could begin to occur, the alternating ultrasound waveform 56 switches from one wave form to the other. This variation in sonic waveform ultrasound minimizes any chance of damage to the compound or to the patient's skin or underlying tissue.

Applicant discovered that the depth of penetration of the compound 54 can be affected by carefully selecting the duration and relative duration of each waveform type to determine an appropriate duty cycle. In the case of acne treatment, where the goal is not to have the compound penetrate below the epidermis layer 12, the duty cycle of the ultrasonic signal may be a loop of approximately 80 milliseconds sawtooth waveform, followed by approximately 20 milliseconds square waveform, which order is then repeated sequentially. Variations from the durations of these waveforms and the ratio of the duration therebetween are possible within the scope of this invention. For example, the duration of the first predetermined period for the sawtooth waveform 58 could be at least twice the duration of the second predetermined period for the square waveform 60. In another example, the duration of the first predetermined period for the sawtooth waveform 58 could be at least four times the duration of the second predetermined period for the square waveform 60. A longer duration for the square waveform 60 results in an increased depth of penetration for the compound into the skin tissue and a faster delivery rate thereof. Using the above-mentioned duty cycle, Applicants have found that deposition of acne medication into pores 41 can take place in as little as 10 seconds of ultrasound exposure. For those patients with more severe acne, the duration of the square waveform 60 portion of the alternating ultrasound waveform 56 may be increased in order to provide greater sonic vibration to the pores 41 in order to affect evacuation of oils from deep within the affected tissue, and to push the compound deeper into the pores 41.

With reference to FIGS. 8-11, one embodiment of an ultrasound device 62 will now be described in detail. In this embodiment, the ultrasound device 62 is a hand-held, wireless electronic device. The device 62 comprises a housing 64 having an activation control 66 and an indicator lamp 68 that lets the user know when the device 62 is active. An activation receiver 76 on the housing 64 mates with and connects to an activation tab 74 located on a patch cap 70, which will be described in further detail below. U.S. Pat. No. 6,908,448, the entire contents of which are incorporated herein by reference, teaches one example of an ultrasonic device for delivering compounds.

Figure 11:
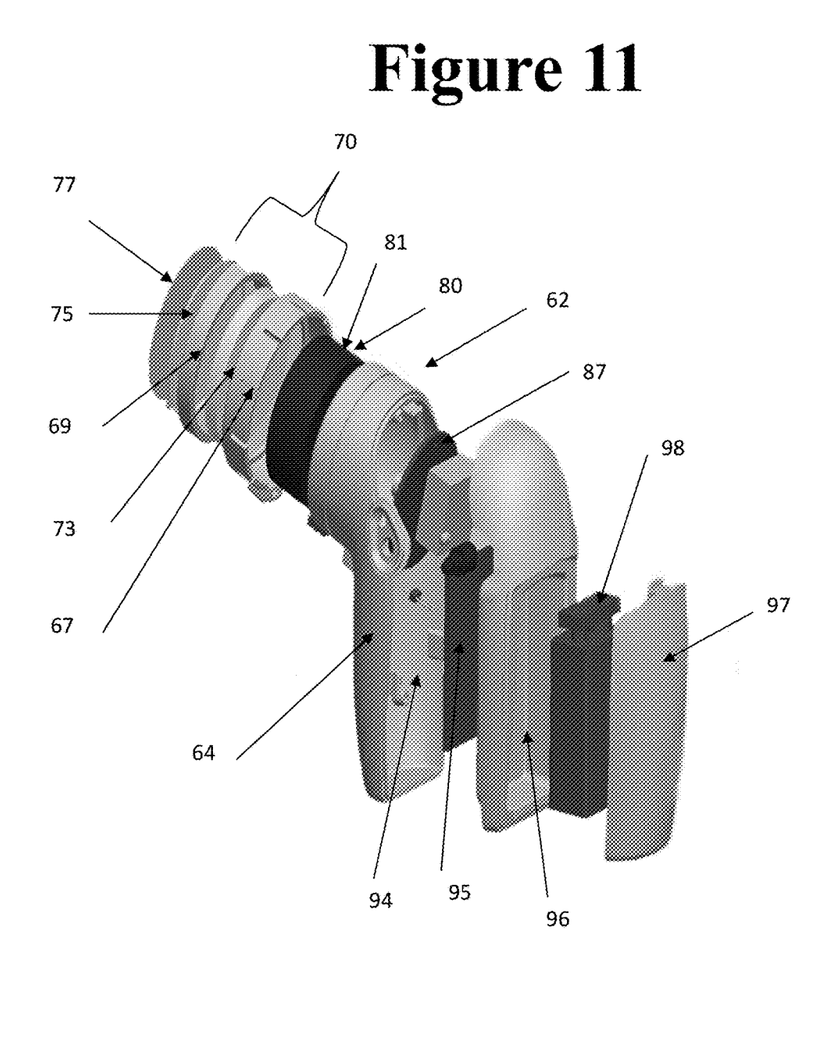

Patch cap 70 has a housing 67, snap-on tabs 71 that enable it to snap onto the housing 64 of the device 62, and a perforated film layer 75 having a fabric center 72. A peel-away film 77 is initially provided on the patch cap 70 for sanitary purposes. The patch cap 70 may be made to be reusable or disposable after each use. When the patch cap 70 is properly mounted on the housing 64, the activation tab 74 connects with the activation receiver 76. The device is designed not to operate unless the activation tab 74 and activation receiver 76 are properly engaged. The patch cap 70 is the component of the device 62 that comes into direct contact with the patient's skin. As best seen in FIG. 11, patch cap also includes a cream storage drum 73 having a sonic membrane (not labeled) at the bottom thereof, a foam ring 69, a perforated film layer, and a peel-away film at the outermost end thereof.

Figure 10:
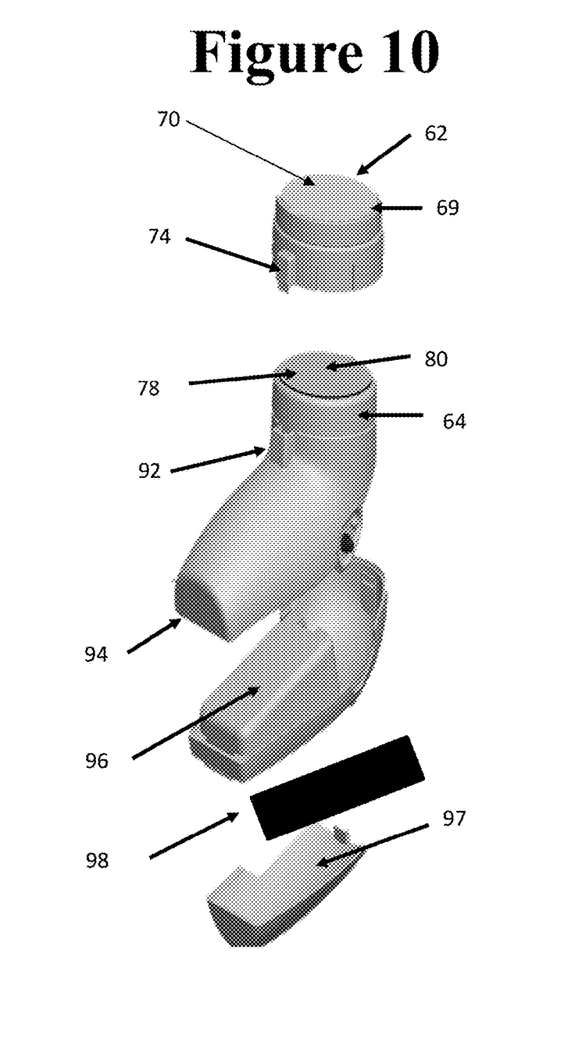

FIGS. 10 and 11 are partial exploded views of the device 62, showing some of its internal components. As seen in these Figures, the device 62 further comprises the main housing piece 64, a battery compartment 96 that holds a battery 98 (which, in this embodiment, is a 9V battery), and a battery cover 97. The electronics of the device, which are not shown or described herein in detail but include circuit board set 95, are located within a circuit compartment 94 of the housing 64.

Figure 12:
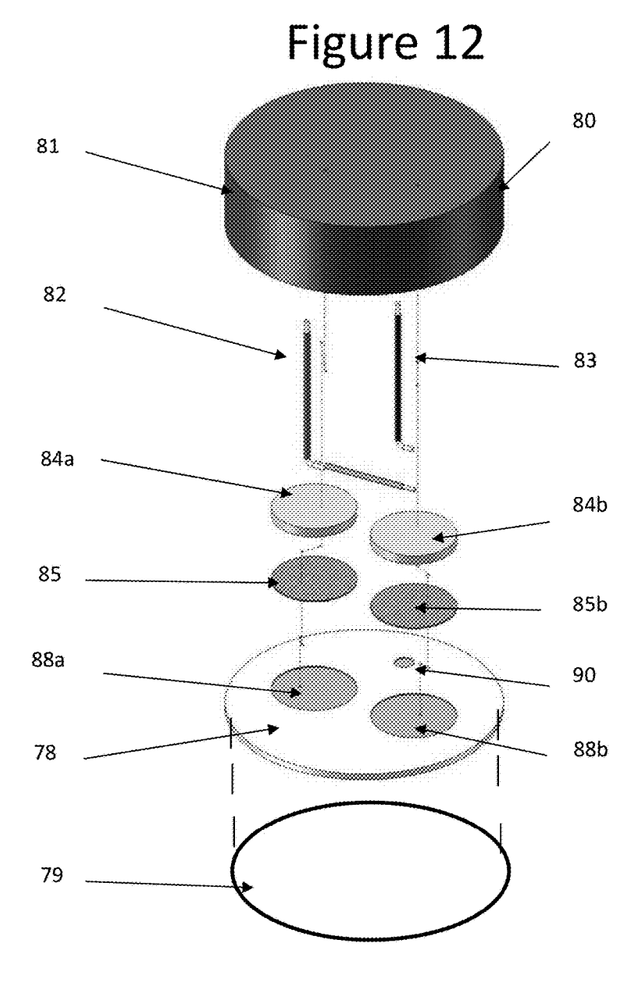
Figure 13:
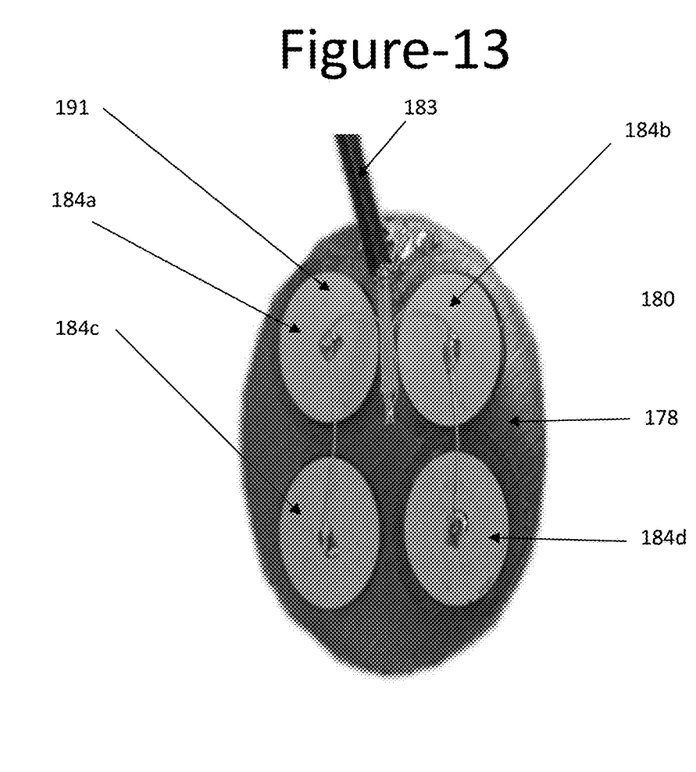

A transducer array 80, which will be described in greater detail below, is placed at the head portion of the device 62, and then covered with the patch cap 70. FIGS. 12 and 13 show two embodiments of transducer arrays. In FIG. 12, transducer array 80 comprises a block 81, which in some embodiments is made of nylon, and a face plate 78, which in some embodiments is made of stainless steel. The block 81 acts to reflect the acoustic waves that are generated by the transducer discs 84a, 84b so that the amount of acoustic energy that travels in the direction of the face plate 78 is maximized. The transducer discs 84a, 84b may be constructed of piezoelectric, magnetorestrictive, or cymbal triple transducer discs. A live wire 82, which is insulated, connects the transducer discs 84a, 84b together, and also connects to the electronics of the device 62 so that the transducer discs 84a, 84b can receive power and the appropriate electrical signal, which is then converted into mechanical force in the form of acoustic waveforms as discussed herein. A ground wire 83 is connected to a solder point 90 located on the face plate 78. The transducer discs 84a, 84b are affixed in a respective one of a pair of depressions 88a, 88b on the surface of the face plate 78 using a respective one of a pair of conductive epoxy layers 85a, 85b. In the alternative, the transducer discs 84, 84b could be soldered to the face plate 78. Fitted around the perimeter of the face plate 78 and glued thereto with an epoxy is a ring 79, which in some embodiments is made of a neoprene rubber. Neoprene foam rings provide excellent moisture protection for the transducer discs 84a, 84b while also affording flexibility to the face plate 78 to enable it to move in resonance response to the mechanical energy produced by the transducer discs 84a, 84b.

FIG. 13 shows a second embodiment of a transducer array 180. In this embodiment, four transducer discs 184a-d are provided on the face plate 178. In this embodiment, a bridge wire 191 connects the four transducer discs 184a-d together, and a ground wire 183 is soldered directly to the face plate 178. It should be understood that the transducer array 180 may be incorporated into the ultrasonic device as otherwise disclosed herein.

Some preferred embodiments of the ultrasonic applicator device have specific operating parameters, as shown in the Table below:
TABLE-US-00001 Range of Settings: Ideal Settings: Frequency: 20-30 kHz 23 kHz Intensity per Transducer Disc 75-150 mW/sq·cm 125 mW/sq·cm Element: No of Transducer Discs in 1-4 2 Wand Device: Combined intensity (Power Up to 500 mW/sq·cm 250 mW/sq·cm Output):

Example

Figure 14A:
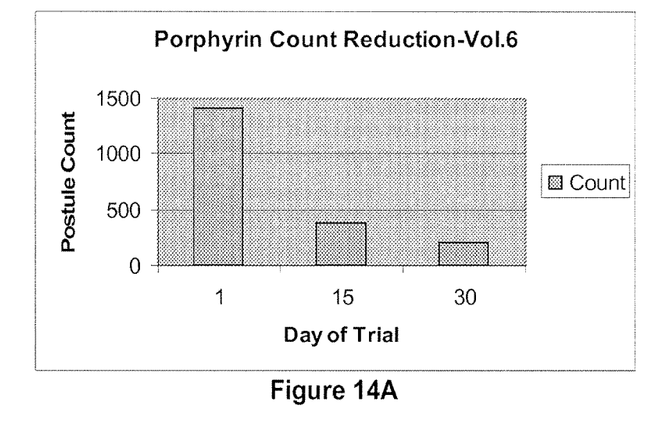
Figure 14B:
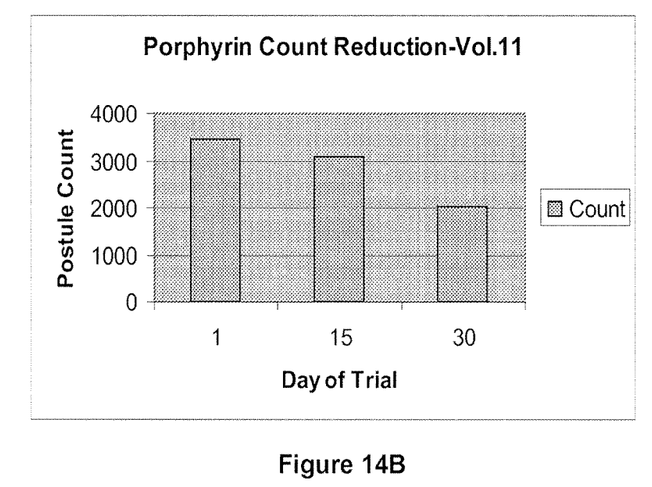
Figure 14C:
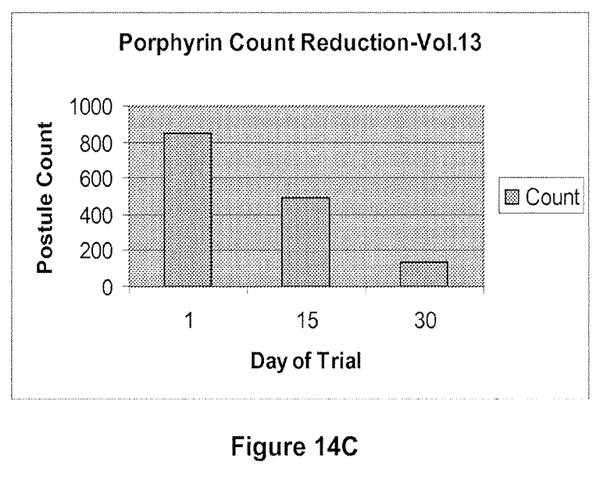

FIGS. 14A-14C show facial porphyrin count reduction for three different teenaged volunteers that used an ultrasound device according to the present invention in conjunction with a bactericide. For all three individuals, postule counts dropped dramatically between Day 1 and Day 15 of the Trial, and again between Day 15 and Day 30 of the Trial. Average acne lesion reduction for these three volunteers between Day 1 and Day 15 of the Trial was approximately 42%, and between Day 1 and Day 30 of the Trial was approximately 70%.

While the principles of the invention have been described above in connection with preferred embodiments, it is to be clearly understood that this description is made only by way of example and not as a limitation of the scope of the invention.

I claim:

1. An ultrasonic transducer assembly comprising a face plate (78), at least one ultrasonic transducer (84) by which electrical energy is converted to acoustic energy and having first and second opposed major surfaces, the first major surface being attached to the face plate, a live electrical lead connected to the ultrasonic transducer and adapted for connection to a source of electricity, a block adjacent the second opposed major surface of the ultrasonic transducer to reflect the acoustic energy from the ultrasonic transducer in the form of acoustic waveforms toward the face plate, a ground electrical lead attached to the face plate and adapted for connection to a ground connection, and a peripheral gasket attached to the face plate and to the block to protect the ultrasonic transducer between the faceplate and the block from moisture.

2. The ultrasonic transducer assembly of claim 1, further comprising a plurality of ultrasonic transducers attached at first major surfaces to the face plate, the plurality of ultrasonic transducers being connected by at least one bridge wire to the live electrical lead.

3. The ultrasonic transducer assembly of claim 2, wherein there are two ultrasonic transducers attached to the face plate.

4. The ultrasonic transducer assembly of claim 2, wherein there are four ultrasonic transducers attached to the face plate.

5. The ultrasonic transducer assembly of claim 1, wherein the at least one ultrasonic transducer is soldered to the face plate.

6. The ultrasonic transducer assembly of claim 1, wherein the at least one ultrasonic transducer is attached to the face plate by conductive epoxy.

7. The ultrasonic transducer assembly of claim 1, wherein the at least one ultrasonic transducer is attached to at least one depression formed in the face plate by conductive epoxy.

8. The ultrasonic transducer assembly of claim 1, wherein the at least one ultrasonic transducer is construction selected from the group consisting of a piezoelectric material, a magnetorestrictive material and a cymbal triple construction.

9. The ultrasonic transducer assembly of claim 1, wherein the face plate is stainless steel.

10. The ultrasonic transducer assembly of claim 1, wherein the block is nylon.

11. The ultrasonic transducer assembly of claim 1, wherein the peripheral gasket is neoprene foam rubber adhesively attached to the face plate and to the block.

12. The ultrasonic transducer assembly of claim 1, wherein the at least one ultrasonic transducer is a disc, the face plate is a stainless steel disc, the at least one ultrasonic transducer is attached to the face plate stainless steel disc by conductive epoxy, the block is a disc of nylon, and the peripheral gasket is a neoprene foam rubber adhesively attached to the face plat and to the block.

13. The ultrasonic transducer assembly of claim 1, further comprising a plurality of ultrasonic transducers attached at first major surfaces to the face plate, the plurality of ultrasonic transducers being connected by at least one bridge wire to the live electrical lead.

14. The ultrasonic transducer assembly of claim 13, wherein there are two ultrasonic transducers attached to the face plate.

15. The ultrasonic transducer assembly of claim 14, wherein there are four ultrasonic transducers attached to the face plate.

16. Apparatus comprising the ultrasonic transducer assembly of claim 1 and a driving circuit, the apparatus being operationally configured to emit an ultrasonic waveform that alternates between a first waveform and a second waveform, both the first waveform and the second waveform being non-sinusoidal.

17. The apparatus of claim 16, wherein the first waveform is a sawtooth waveform and the second waveform is a square waveform.

18. The apparatus of claim 16, wherein the first waveform has a first predetermined period and the second waveform has a second predetermined period, the first and second predetermined periods being of different duration.

19. The apparatus of claim 18, wherein the duration of the first period is at least twice the duration of the second period.

20. The apparatus of claim 18, wherein the duration of the first period is at least four times the duration of the second period.

21. The apparatus of claim 18, wherein the duration of the first period is approximately 80 milliseconds and the duration of the second period is approximately 20 milliseconds.

\* \* \* \* \*